United States Patent
Coppedè et al.

(10) Patent No.: US 11,344,230 B2
(45) Date of Patent: May 31, 2022

(54) WEARABLE TECHNOLOGY WITH SENSORS INTEGRATED INTO CLOTHING FIBERS

(71) Applicant: HFT Smart Sensors, Incorporated, Rockford, IL (US)

(72) Inventors: Nicola Coppedè, Parma (IT); Andrea Zappettini, Reggio Emilia (IT)

(73) Assignee: HFT Smart Sensors, Incorporated, Rockford, IL (US)

( * ) Notice: Subject to any disclaimer, the term of this patent is extended or adjusted under 35 U.S.C. 154(b) by 785 days.

(21) Appl. No.: 15/942,658

(22) Filed: Apr. 2, 2018

(65) Prior Publication Data

US 2018/0279930 A1  Oct. 4, 2018

Related U.S. Application Data

(60) Provisional application No. 62/480,951, filed on Apr. 3, 2017.

(51) Int. Cl.
*A41B 1/08* (2006.01)
*A42B 3/10* (2006.01)
(Continued)

(52) U.S. Cl.
CPC ............ *A61B 5/14517* (2013.01); *A41B 1/08* (2013.01); *A41D 31/12* (2019.02); *A42B 3/10* (2013.01);
(Continued)

(58) Field of Classification Search
CPC . A61B 5/14517; A61B 5/1477; A61B 5/6804; A61B 5/1486; A61B 5/6805;
(Continued)

(56) References Cited

U.S. PATENT DOCUMENTS 5,312,667 A     5/1994 Lumb et al.
2017/0027481 A1*  2/2017 Coppede' ............ A61B 5/1486

FOREIGN PATENT DOCUMENTS

EP         3 045 902 A1   7/2016
WO    WO 2012/150487 A1  11/2012

OTHER PUBLICATIONS

Nicola Coppedè et al., "Human stress monitoring through an organic cotton-fiber biosensor", Journal of Materials Chemistry B, vol. 2, No. 34, Jun. 10, 2014, p. 5620-5621.
(Continued)

*Primary Examiner* — Jenna L Johnson
(74) *Attorney, Agent, or Firm* — Reinhart Boerner Van Deuren P.C.

(57) ABSTRACT

Embodiments of the invention disclosed herein are directed to articles of clothing that allow for monitoring of different analytes (e.g., electrolytes and molecules) in human sweat during fitness activity, while training, or simply in everyday life. The clothing includes a sensor system completely integrated in textile such that every sensing part is made of textile fibers. The clothing is able to control, collect, analyze, and expel the sweat over time. The textile sensor allows a spontaneous absorption of body sweat directly from the skin, while it is produced, using the hydrophilic natural properties of the textile. Then, once adsorbed, the flux of sweat is controlled and guided through the textile using a gradient of the textile's hydrophilic properties. The sweat guided through the textile is analyzed through an electrochemical sensor woven into the textile. Finally, the sweat is collected in a reservoir and expelled for evaporation.

16 Claims, 10 Drawing Sheets

(51) Int. Cl.
| | |
|---|---|
| D04B 1/12 | (2006.01) |
| A41D 31/12 | (2019.01) |
| D03D 15/283 | (2021.01) |
| A61B 5/145 | (2006.01) |
| D02G 3/44 | (2006.01) |
| D02G 3/36 | (2006.01) |
| D02G 3/04 | (2006.01) |
| D02G 3/12 | (2006.01) |
| D04B 1/16 | (2006.01) |
| D04B 1/14 | (2006.01) |
| D04B 1/24 | (2006.01) |
| C12Q 1/00 | (2006.01) |
| G01N 33/487 | (2006.01) |
| A61B 5/1486 | (2006.01) |
| A61B 5/1477 | (2006.01) |
| A61B 5/00 | (2006.01) |
| D03D 15/25 | (2021.01) |
| G01N 27/327 | (2006.01) |
| A42B 3/04 | (2006.01) |
| A41D 1/00 | (2018.01) |
| D03D 15/533 | (2021.01) |
| D03D 1/00 | (2006.01) |

(52) U.S. Cl.
CPC ......... *A61B 5/1477* (2013.01); *A61B 5/1486* (2013.01); *A61B 5/6804* (2013.01); *C12Q 1/002* (2013.01); *D02G 3/04* (2013.01); *D02G 3/12* (2013.01); *D02G 3/36* (2013.01); *D02G 3/441* (2013.01); *D02G 3/444* (2013.01); *D03D 15/25* (2021.01); *D03D 15/283* (2021.01); *D04B 1/12* (2013.01); *D04B 1/123* (2013.01); *D04B 1/14* (2013.01); *D04B 1/16* (2013.01); *D04B 1/24* (2013.01); *G01N 33/48707* (2013.01); *A41B 2400/60* (2013.01); *A41B 2500/10* (2013.01); *A41B 2500/20* (2013.01); *A41D 1/002* (2013.01); *A42B 3/0433* (2013.01); *A61B 5/14532* (2013.01); *A61B 5/14546* (2013.01); *A61B 5/6805* (2013.01); *D03D 1/0088* (2013.01); *D03D 15/533* (2021.01); *D10B 2101/20* (2013.01); *D10B 2401/021* (2013.01); *D10B 2401/022* (2013.01); *D10B 2401/16* (2013.01); *D10B 2403/02431* (2013.01); *D10B 2501/04* (2013.01); *D10B 2501/042* (2013.01); *D10B 2509/00* (2013.01); *G01N 27/3271* (2013.01); *Y10T 442/313* (2015.04); *Y10T 442/3976* (2015.04)

(58) Field of Classification Search
CPC  A61B 5/14546; A61B 5/14532; C12Q 1/002; G01N 33/48707; G01N 27/3271
See application file for complete search history.

(56) References Cited

OTHER PUBLICATIONS

Anil Modali et al., "Wearable Woven Electrochemical Biosensor Patch for Non-invasive Diagnostics", Electroanalysis, vol. 28, No. 6, May 23, 2016, pp. 1276-1282.

Christian Müller et al., "Woven Electrochemical Transistors on Silk Fibers", Advanced Matter, Wiley—V C H Verlag GmbH & Co. KGAA, DE, vol. 23, No. 7, Dec. 20, 2010, pp. 898-901.

Mahiar Hamedi et al., "Fiber-Embedded Electrolyte-Gated Field-Effect Transistors for e-Textiles", Advanced Materials, vol. 21, No. 5, Dec. 4, 2008, pp. 573-577.

Zekra Mousavi et al., "Ion-Selective Organic Electrochemical Junction Transistors Based on Poly(3,4-ethylenedioxythiophene) Doped with Poly(styrene sulfonate)", Electroanalysis, vol. 21, No. 3-5, Jan. 16, 2009, pp. 472-479.

I. Gualandi et al., "Textile Organic Electrochemical Transistors as a Platform for Wearable Biosensors", Scientific Reports, vol. 6, No. 1, Sep. 26, 2016, pp. 1-8.

Coyle et al.; BIOTEX-Biosensing Textiles for Personalised Healthcare Management; IEEE Transactions on Information Technology in Biomedicine, vol. 14. No. 2. Mar. 2010; 7 pages.

Yahui Yang et al.; Wearable microfluidics: fabric-based digital droplet flowmetry for perspiration analysis; Royal Society of Chemistry; Lab Chip, 2017, 17, 926; 10 pages.

Tarabella et al.; A single cotton fiber organic electrochemical transistor for liquid electrolyte saline sensing; J. Mater. Chem., 2012, 22, 23830.

* cited by examiner

| PRODUCT | TEXTILE SENSING SYSTEM | GENERAL SENSOR FOR ALL ELECTROLYTES | SELECTED SENSORS | SUBSTANCES REVEALED |
|---|---|---|---|---|
| -T-SHIRT<br>-SMART BAND<br>-HELMET | APP FOR MONITORING PERFORMANCES<br>BLUE TOOTH COMMUNICATION WITH CELL PHONE<br>READING AND TRANSMITTING ELECTRONICS<br>PRIVATE CLOUD DATABASE<br>ALGORITHM TO ANALYZE AND IMPROVE HEALTH, TRAINING AND PERFORMANCE | SYSTEM TO REALIZE GRADIENT ABSORPTION OF FLUIDS<br>-GRADIENT OF DENSITY<br>-GRADIENT OF MATERIALS (FROM HYDROPHILIC TO HIGH HYDROPHILIC)<br>-PERCENTAGE OF SINTHETIC IN THE FIBERS<br>GRADIENT ABSORBING TEXTILE SENSOR<br>TYPE OF SENSOR<br>-ORGANIC ELECTROCHEMICAL TRANSISTOR (PREFERRED)<br>-POTENTIOMETRIC<br>-AMPEROMETRIC | SENSOR IN GRADIENT TEXTILE WITH ION SELECTIVE MEMBRANE<br>{USE OF SILANE MOLECULE TO EMBEDD ENZYME}<br>SENSOR IN GRADIENT TEXTILE WITH EMBEDDED ENZYME<br>SENSOR IN GRADIENT TEXTILE WITH DNA STRAND OR PROTEIN<br>SENSOR WITH CATALYTIC ELECTRODE (PT) | Na, K, Ca, Mg<br><br>GLUCOSE, LACTATE, UREA, DOPAMINE, TYROSINE<br>SPECIFIC BACTERIA<br>ADRENALINE |

FIG. 17

WEARABLE TECHNOLOGY WITH SENSORS INTEGRATED INTO CLOTHING FIBERS

CROSS-REFERENCE TO RELATED PATENT APPLICATION

This patent application claims the benefit of U.S. Provisional Patent Application No. 62/480,951, filed Apr. 3, 2017, the entire teachings and disclosure of which are incorporated herein by reference thereto.

FIELD OF THE INVENTION

This invention generally relates to functionalized clothing and, more particularly, to clothing that senses the contents of the sweat of a wearer.

BACKGROUND OF THE INVENTION

During activity, humans produce sweat. Sweat contains electrolytes and other molecules that the body excretes during times of activity. These electrolytes and other molecules are important indicators of the nutrient and hydration levels of the person performing the activity.

BRIEF SUMMARY OF THE INVENTION

The invention provides a textile wearable by a user that includes sensors for monitoring the levels of electrolytes and other molecules in sweat. The textile is engineered to create a sweat flux to transport fresh sweat to the sensors for analysis and remove old sweat from the sensor region such that relevant results are continually provided. These and other advantages of the invention, as well as additional inventive features, will be apparent from the description of the invention provided herein.

In one aspect, a textile with integral sensors is provided that allows for the spontaneous absorption of sweat in the textile fibers so as to advantageously allow for measurement of analyte levels using non-direct contact with the skin. The textile is provided with a hydrophilic gradient so that an accumulation of fluid produced over time does not render the analysis unreliable, i.e, new sweat is not constantly added to the old sweat for analysis. Thus, embodiments of the presently disclosed textile allow the effective control of the sweat analyzed, monitoring of sweat during time, and correlation of the results of the analysis with the physiological state of the wearer over time.

In another aspect, the textile includes an integrated sensor formed from a fiber that has been functionalized with a conductive polymer. The functionalized fiber acts as a channel between a source electrode and a drain electrode. Another fiber, such as a metal fiber or wire, is provided and is connected to gate electrode. The gate electrode is biased with a positive voltage while a negative voltage is applied across the source and drain electrode. After being transported to the sensor by a hydrophilic gradient in the textile, positive ions in the sweat reversibly affect the conductivity of the conductive polymer in the functionalized fiber in response to the gate voltage. In this way, the response of the functionalized fiber can be measured to determine the concentration of the positive ions in the sweat.

In a further aspect, the sensors integrated into the textile are selective such that the sensors will only detect the presence of specific ions. In certain embodiments, the sensors are surrounded by an ion selective membrane, such that only certain ions are allowed to pass through to the conductive polymer. In other embodiments, the sensors include enzymes that are entrapped around the conductive polymer such that only reactions with specific molecules will trigger the release of ions to interact with the conductive polymer. In still another embodiment, DNA strands are bonded to the sensor such that the DNA strands will react with the DNA of other organisms, such as bacteria, to determine the presence of these organisms.

These sensor integrated textiles can be incorporated into clothing (such as shirts), bands, or helmets so as to passively collect the sweat of the wearer. The information detected by the sensors can be exported to a mobile application and/or to a cloud service for recordation and analysis. In this way, the wearer or another observer can monitor the hydration and nutrient levels of the wearer during activity.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Embodiments of the invention disclosed herein are directed to articles of clothing that allow for monitoring of different analytes (e.g., electrolytes and molecules) in human sweat during fitness activity, while training, or simply in everyday life. The clothing includes a sensor system completely integrated in textile such that every sensing part is made of textile fibers. The clothing is able to control, collect, analyze, and expel the sweat over time. The textile sensor allows a spontaneous absorption of body sweat directly from the skin, while it is produced, using the hydrophilic natural properties of the textile. Then, once absorbed, the flux of sweat is controlled and guided through the textile using a gradient of the textile's hydrophilic properties. The sweat guided through the textile is analyzed through an electrochemical sensor woven into the textile. Finally, the sweat is collected in a reservoir and expelled for evaporation.

To correctly measure the concentration of different analytes in sweat over time, to monitor the physiological condition and the performances, it is mandatory to control the absorption of sweat in real time. Indeed, preferably only fresh body sweat is analyzed to avoid inaccurate measurements caused by mixing fresh body sweat and old body sweat. Further, to provide affordable monitoring of the sweat characteristics, the analyte concentrations are measured as the sweat is produced. If, instead, a sensor is simply applied on the skin, the accumulation of the sweat creates a gradual increase (i.e., buildup) of the electrolytes, thereby resulting in an inaccurate picture of the current sweat condition. The overall effect of a non-controlled accumulation of the sweat is that measurements in time lose any significance regarding the actual status of the subject. In order to provide a sensor that is able to monitor electrolytes and other molecules in sweat in real time, the sweat sample must be controlled in quantity, position, and timing in such a way as to perform significant measurements.

Advantageously, the textile sensor system can be worn in comfort without the wearer sensing it because it is made of the same material as common clothes. Additionally, the textile sensor system can naturally absorb the sweat because of the natural hydrophilic properties of the fibers. Further, the textile sensor system can control the flux of sweat without mixing sweat produced at different times and in different regions of the clothing. Still further, the textile sensor system can analyze different electrolytes and molecules using sensors integrated into the textile fibers in different geometries and configurations.

Broadly, the monitoring system includes a sensing textile system, integrated electronic board for reading and live data transmission, reading software, an application for a cellular phone to read live the measurements, private cloud database to collect and elaborate all the data, big data analysis system, to give live advice and suggestion for an optimized training and hydration.

Generally, the invention exploits the capillary properties of a textile by utilizing different surface tensions on the textile (using different approaches described hereinbelow) to gradually change the textile's hydrophilic properties in such a way as to build a forced pathway for the sweat. This creates a way to perform measurements while sweat is absorbing and moving in a fixed direction in the textile. Exploiting the absorption from inside to the outside of the textile and/or from the top to the bottom, it is possible to create a pathway that controls quantity, position, and timing of the sweat flow. In this way, it is possible to distinguish the newly generated sweat from the older sweat, thereby avoiding uncontrolled accumulations. Combining a textile sensor with a gradient in absorption provides a sensor system that is able to monitor fluids in real time.

The textile utilizes interfacial principles and implements liquid transport spontaneously based on the properties of the fabric and by using surface tension force in addition to the intrinsic capillary force in hydrophilic fibers. Body fluid removal is facilitated through a well-controlled flow rate and removal rate. The gradient in wettability provides liquid removal and transport. According to the following embodiments, an interfacial change in density and hydrophilicity establishes three-dimensional liquid flows into the textile volume. In particular, the interfacial microfluidic transport utilizes the surface tension-induced pressure gradient along the flow path defined by extreme wetting contrast to facilitate the liquid motion in the textile network. The wetting contrast patterns are defined by stitching patterns of hydrophilic yarns (water contact angle of 0°) on the hydrophobic (e.g., acrylic) textile. The hydrophobic textile could also be superhydrophobic (i.e., water contact angle of $\geq 140°$). Superhydrophobicity can be obtained by coating the textiles with a thin layer of fluoropolymer or silica nano- or microparticles. The transport duration can be highly-controlled by the dimensions of the hydrophilic pattern (inlet and outlet) and connecting yarns (channel).

U.S. Pat. No. 5,312,667, incorporated herein in its entirety by reference, discloses a composite fabric suitable for use in embodiments of the present invention. The composite fabric includes a first fabric layer comprising either a polyester or nylon material whose surface has been raised and which has been rendered hydrophilic. The composite fabric also includes a second fabric layer comprising at least 35% by weight of a moisture absorbent material (such as cotton). The first fabric layer and the second fabric layer are formed concurrently by knitting a plaited construction so that the layers are distinct and separate yet integrated with each other.

Figure 1:
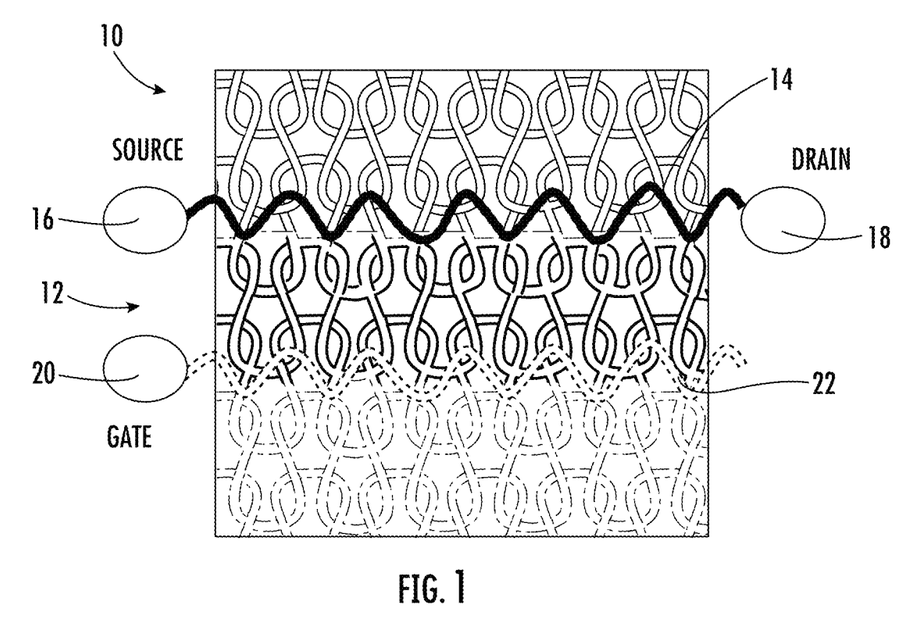
FIG. 1 depicts a textile with an integrated sensor according to an exemplary embodiment.

FIG. 1 provides an exemplary embodiment of a textile 10 that has been functionalized to transport sweat and analyze its content. As shown in FIG. 1, the different line styles of the textile 10 represent areas with increasing hydrophilic properties, i.e., hydrophilicity increases going from top to bottom in FIG. 1. An electrochemical transistor sensor 12 is woven into the textile. In particular, a fiber 14 functionalized with a conductive polymer is present between a source electrode 16 and a drain electrode 18. A gate electrode 20 includes a fiber 22 based on textile functionalized with metal deposition, or with metal microparticle, or with conducting polymer (similar to the channel between source and drain), or simple a thin metal wire (such as Ag, Pt, Au, Cu, etc., depending on the application) or a carbon fiber. In this way, when fluid is absorbed by the textile 10, the transistor electrodes 16, 18, 20 woven into the textile 10 work like an electrochemical transistor sensor. The potential at the gate electrode 20 forces the positive ions to move to the polymer fiber 14. The potential between source 16 and drain 18 generates a current that depends on the properties of the conductive polymer in fiber 14. The current changes proportionally to the number of positive ions that are forced to enter into the conductive polymer of fiber 14 (the proportion is based on the specific properties of the conductive polymer chosen for fiber 14). Thereby, calculating the changes in the polymer current, it is possible to measure the concentration of the positive ions in the fluid as will be explained in more detail below. Embodiments of the invention operate in accordance with the disclosure of 163605 IT, the contents of which are incorporated by reference herein in their entireties.

The fiber 14 functionalized with a conductive polymer (transistor channel) can be formed from a textile fiber (e.g., cotton, silk, synthetic) that has been functionalized with a conductive polymer such as poly(3,4-ethylenedioxythiophene) ("PEDOT"), poly(6-(thiophene-3-yl)ethane-1-sulfonate (PTHS), polyaniline, polypyrrole, polythiophene, and polyfuran. Preferred polymers for functionalizing the textile fiber include PEDOT:PSS (poly(3,4-ethylenedioxythiophene) polystyrene sulfonate) with 5% of ethylene glycol and 0.01-0.05% DBSA or PEDOT:TOS (poly(3,4-ethylenedioxythiophene) tosylate).

As mentioned above, the gate fiber 22 can be a polymer fiber such as those described for fiber 14, a metal based fiber (e.g., Ag, Pt, Au), or a small metal wire.

The following is a description of how the sensor works. A potential (Vds), which can be −0.1V, is applied across the source 16 and drain 18 over the conducting polymer fiber 14, and a current Ids is measured. At the gate electrode 20, a positive potential (Vgs), which is typically +1V, is applied for a period of time (such as 2 minutes), and then Vgs is set to 0V for the same period of time (such as 2 minutes). When the sweat is present in the textile 10 between the two active fibers and with Vgs set at +1V, the positive ions in the sweat are forced to move to the polymer functionalized fiber 14. The conductivity of the polymer is reduced through redox reactions when positive ions enter its surface. The reduction is due to a well-known redox reaction described in literature (J. Mater. Chem. 2012, 22, 23830-23834, the contents of which are incorporated herein in their entireties). The reduction is proportional to the concentration of the positive ions in the fluid, i.e., sweat. When the potential at the gate 20 is set again to 0V, the conductivity of the polymer functionalized fiber 14 returns to its previous value in reversible way.

Based on these variations, the difference in Ids current can be calculated between the time at which gate 20 is switched on and the time at which gate 20 is switched off. The difference, $(Ids-Ids_0)/Ids_0$, is directly proportional to the concentration of the positive ions (i.e., electrolytes) in the sweat. Importantly, the textile 10 fibers, having increasing hydrophilic properties and being between the conductive polymer fiber 14 and gate fiber 22, allow the transport and control of the sweat flux. In each time instant, the ions in the liquid sweat move via the electrostatic forces induced in the textile 10. These ions are the active electrolyte of the sensing device 12 and are constantly moved through the sensing device 12 in real time, allowing an accurate monitoring of the properties of the sweat.

Figure 2:
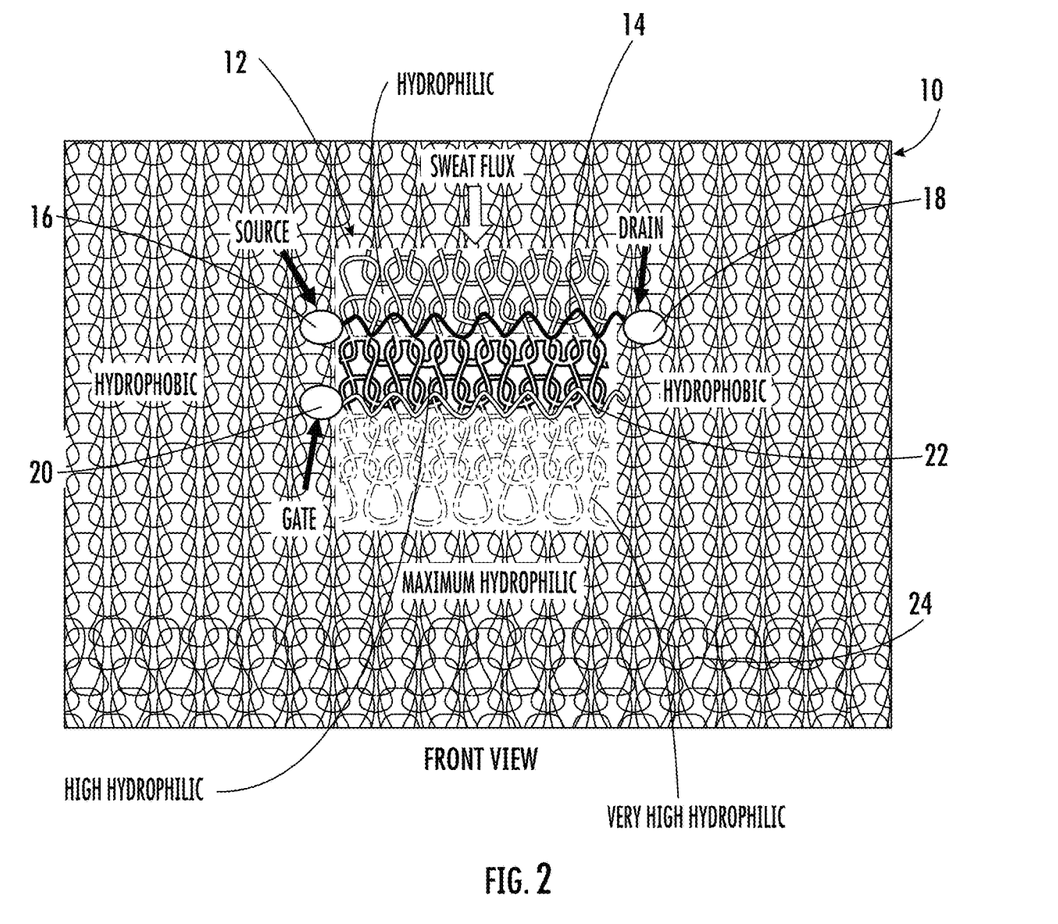
FIG. 2 depicts the textile as shown in FIG. 1 placed in a the context of a larger textile according to an exemplary embodiment.
Figure 3:
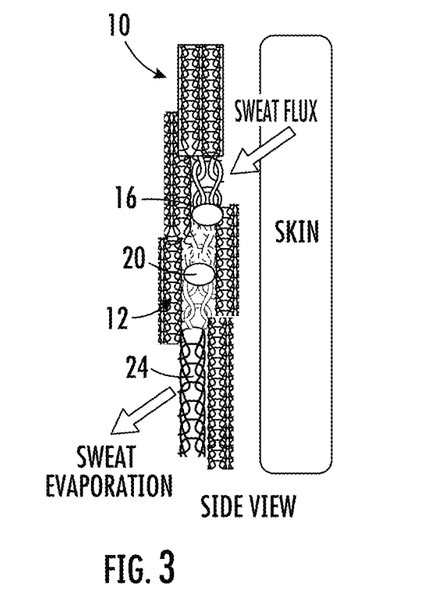
FIG. 3 depicts a side view of the textile of FIG. 2 in relation to the skin of a wearer of the textile.

In FIG. 2, a schematic representation of the integration of the gradient electrochemical transistor sensor is presented. The structure of the textile 10, through the formation of a sweat channel using a gradient of hydrophilicity, allows to the textile 10 to absorb the sweat from a precise area of the skin and guide the to the transistor sensor 12 where the ion content of the sweat is measured. Then the textile 10 facilitates movement of the sweat to a reservoir 24 of the textile 10 having maximum hydrophilicity where it will evaporate. In this way, the flux is guided in two directions: from the top to the bottom (FIG. 2) and from the skin to the outside (FIG. 3). In this way, the flux is guided through a natural pathway to allow evaporation and a controlled measurement of the ion concentrations in the sweat.

Other kinds of sensors can also be integrated in the gradient hydrophilic structure of the textile 10. The sensors can be based on different working principles such as the electrochemical transistor model described above, which allows monitoring of the overall quantity of liquid and the concentrations of positive ions. Further, potentiometric electrochemical measurements can be made by measuring the potential shift after the absorption of the sweat by the textile with respect to a reference electrode, such as Ag/AgCl, instead of a gate. The system could be made of a three electrode structure, one reference electrode of Ag/AgCl as a wire inside the textile, a working electrode and a counter electrode. Common working electrodes can consist of materials ranging from inert metals such as gold, silver or platinum, to inert carbon such as glassy carbon or pyrolytic carbon. Counter electrode could be a textile wire with conducting polymer (PEDOT:PSS) or a textile wire functionalized with specific materials that could react with different elecrolytes in the sweat. Voltammetry measurement can be performed by measuring the change in potential between counter and working electrode and also by measuring with respect to reference electrode, the result of which is proportional to the specific ion concentration. The textile gradient structure device allows absorption and control of the flux of sweat, and the integrated electrodes allow voltammetry measurements. In this way, it is possible to measure different analytes using a textile wearable potentiometric and voltammetric device, such as the measurements of the concentration of a specific ion. In particular, using ion selective membranes, such the one described in the paragraphs below, on the Counter electrode, for example made of textile fiber functionalized with conducting polymer (PEDOT:PSS) and successively covered with the ion selective membrane, it is possible to detect single ions in the sweat ($Na^+$, $K^+$, $Ca^{2+}$, $Mg^{2+}$, etc.).

Figure 4:
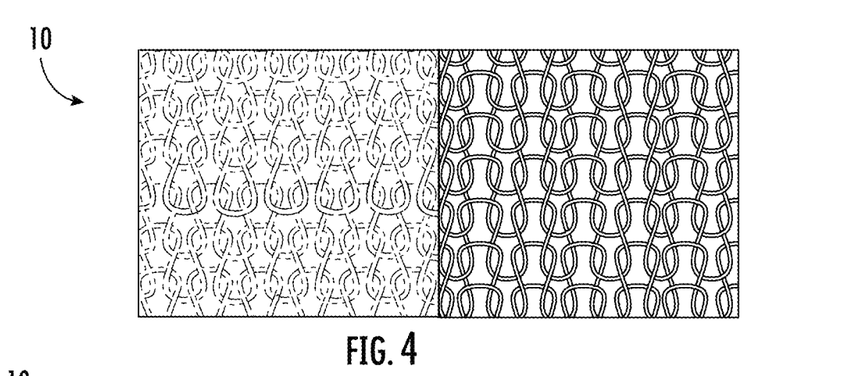
FIG. 4 is depicts a schematic representation of a fiber/knitting arrangement to produce a hydrophilic gradient according to an exemplary embodiment.
Figure 5:
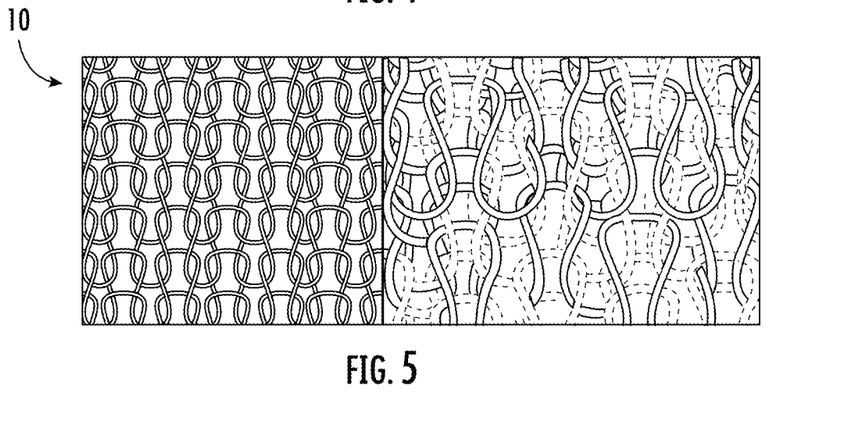
FIG. 5 depicts a schematic representation of a fiber/knitting arrangement to produce a hydrophilic gradient according to an exemplary embodiment.
Figure 6A:
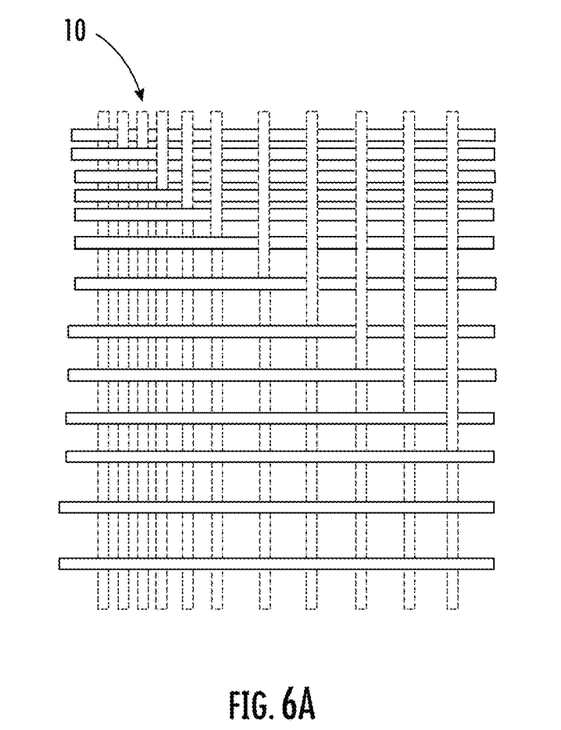
FIGS. 6A-6B depict a schematic representation of a fiber/knitting arrangement to produce a hydrophilic gradient according to an exemplary embodiment.
Figure 6B:
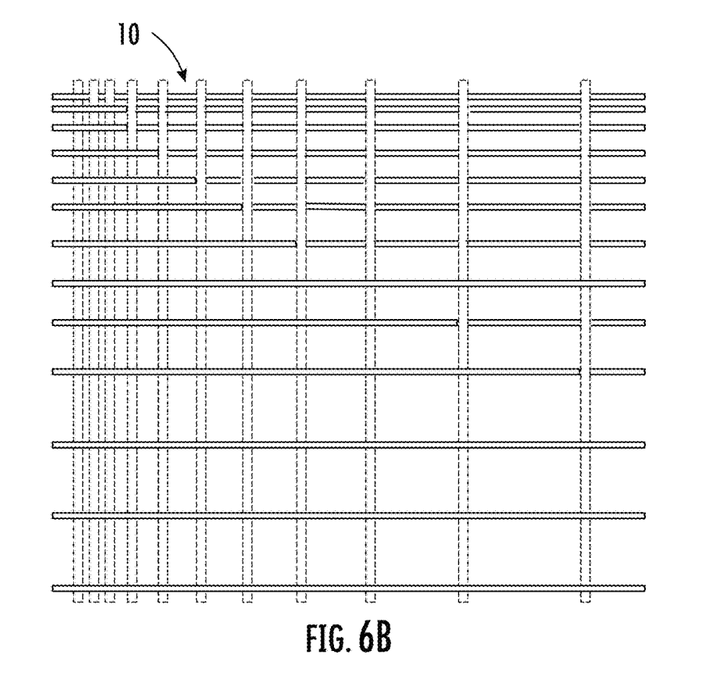

A variety of different mechanisms can be employed to guide the sweat through the textile fabric(s). In particular, a structure with a gradient in hydrophilic properties is preferred. The gradient can be obtained by changing the surface of the textile materials and the density of the textile structure. For example, different textile fiber materials can be knitted into the textile so as to create increasing hydrophilic properties. Specifically, as shown schematically in FIG. 4, the textile fabric transition from acrylic fiber (hydrophobic) to acrylic fiber mixed with cotton fiber (hydrophilic) to cotton fiber alone. Further, the amount of each fiber in different areas of the device can be varied such as by changing the relative amount of each textile fiber. For example, as shown schematically in FIG. 5, the percentage of cotton in the textile can be varied from 10% to 50% to 100% in different areas in such a way as to gradually improve the textile's hydrophilic properties. In another embodiment shown in contrasting FIGS. 6A and 6B, the density of the textile fiber can be manipulated to increase the surface area and the hydrophilic attraction to water molecules. In this way, using a more packed knitting in the textile (FIG. 6A) makes it possible to increase attraction of water based fluids as compared to a less packed knitting (FIG. 6B).

Figure 7:
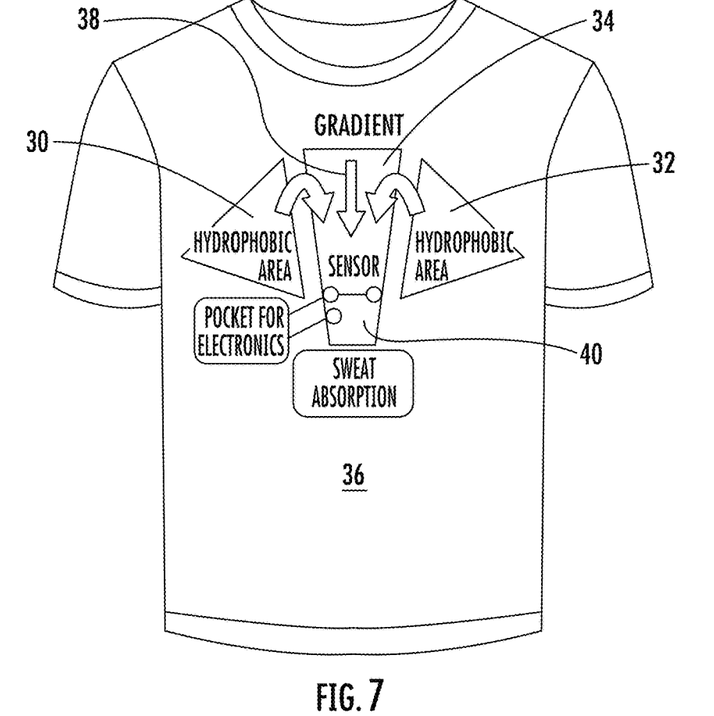
FIG. 7 depicts a garment incorporating the textile with integrated sensor according to an exemplary embodiment.

Embodiments of the textile sensor disclosed herein and based on the aforedescribed technology provide several advantages. In particular, the textile sensor allows for spontaneous absorption of body sweat. Also, the textile controls the flux of body sweat during fitness or physical performances through an architected textile design as depicted schematically in FIG. 7. Control of body sweat flux is obtained by leveraging textile properties, such as hydrophobicity and hydrophilicity. As shown in the FIG. 7, two regions 30, 32 of hydrophobic textile convey body sweat in the central part 34 of a shirt 36. In the central part 34 of the shirt 36, a textile gradient 38 has been designed to gradually increase hydrophilic properties in the textile 10, such as through the methods described above. The sensor 12 has been located at the bottom of the most hydrophilic area of the shirt 36 in a pocket 40 to ensure a gradual absorption of body sweat. As discussed above, a tailored combination of textile fiber types, knitting, and/or coatings forces body sweat to follow an intended flux direction (as denoted by the arrows of FIG. 7) to ensure that only fresh sweat reaches the sensor, thereby avoiding that accumulation of old sweat and providing dynamic monitoring of the wearer's condition.

Figure 8:
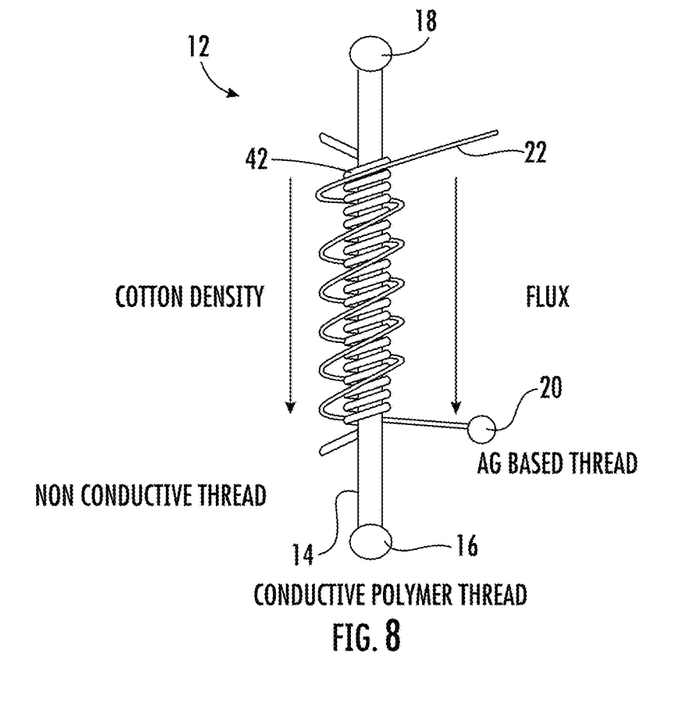
FIG. 8 depicts a wound fiber transistor sensor according to an exemplary embodiment.
Figure 9:
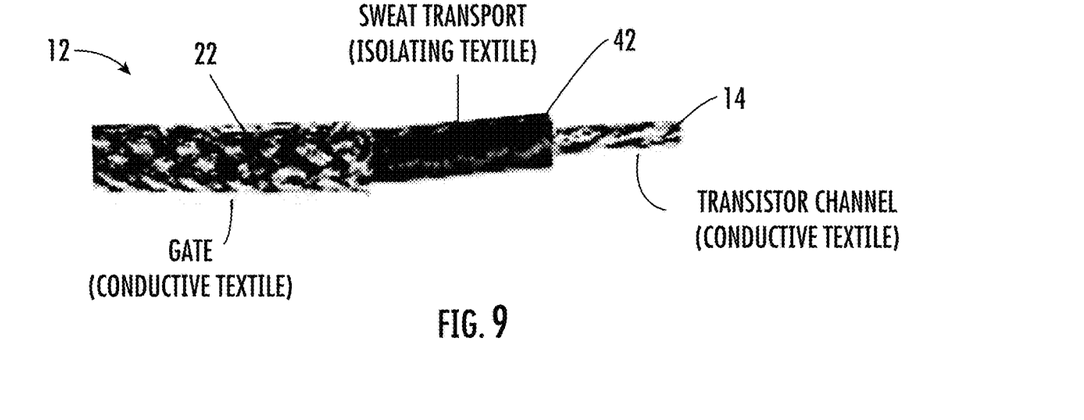
FIG. 9 depicts another embodiment of a wound fiber transistor sensor according to an exemplary embodiment.
Figure 10:
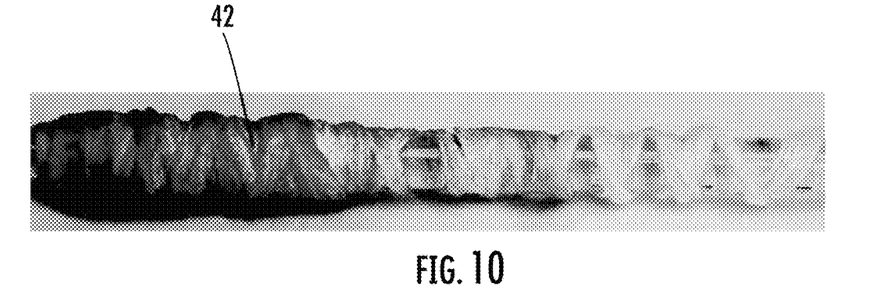
FIG. 10 depicts a fiber winding have varying density along its length according to an exemplary embodiment.

In another embodiment shown in FIG. 8, a sensor 12 is based on the twist of a nonconductive thread 42, having different density along its length, around the polymer functionalized fiber 14 in such a way to create a gradient in density. The source electrode 16 and drain electrode 18 are located on opposite sides of the polymer functionalized fiber 14. The gate electrode 20 is included on a conductive gate fiber 22 that is twisted around the nonconductive thread 42. In this way, the nonconductive fiber 42 is not only able to shield direct contact between the channel fibers 14 and gate fibers 22 but also guides the transport of the sweat flux from top to bottom in the sensor 12 because of the difference in density along its length. The difference in density along the length of the nonconductive fiber 42 winding can be manipulated by varying the number of windings, the distance between windings, the nature of the fiber with increasing hydrophilic properties, etc. FIG. 9 provides an exemplary embodiment in which the nonconductive thread 42, functionalized fiber 14, and gate fiber 22 are all braided fibers in which the nonconductive thread 42 serves as a sheath around the functionalized fiber 14 to isolate it from the gate fiber 22. FIG. 10 depicts a nonconductive thread 42 winding that varies in density by changing the number of windings and distance between windings along the length of the winding.

The sensors disclosed herein have the advantages of being noninvasive as they are fully embedded in the textile and enable the monitoring of several pathologies related to a variety of species. Further, the sensors described above are sensitive to all electrolytes, in particular to cations, and are able to detect their concentration by controlling the flux of the fluid in which they are contained. However, differentiation between cations is important to provide more relevant results. In this regard, selectivity of cations is improved such that a sensor responds only to specific ions in the sensing system.

Figure 11:
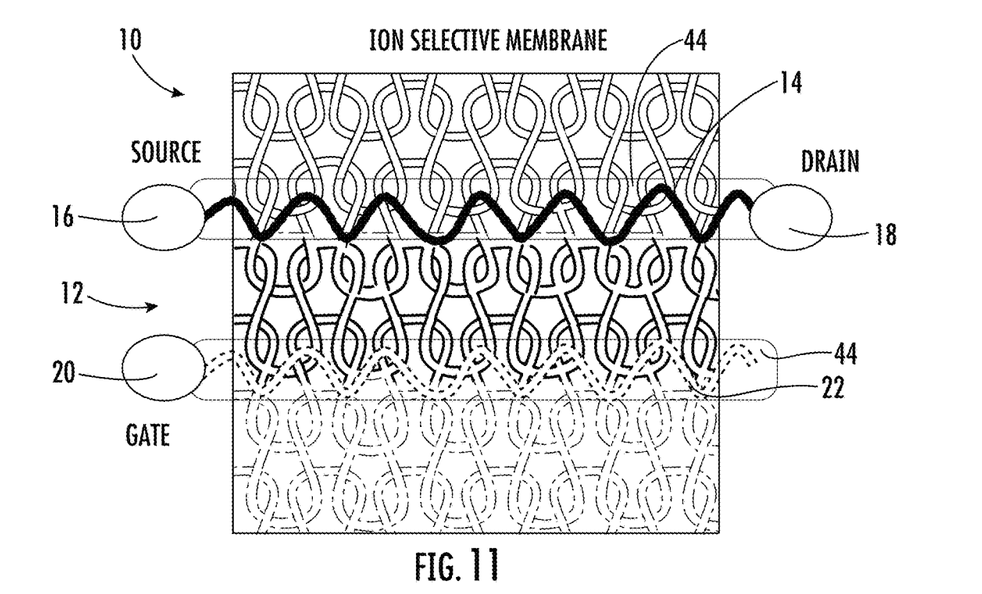
FIG. 11 depicts an ion selective membrane used with a textile having an integrated sensor according to an exemplary embodiment.

As shown schematically in FIG. 11, one way to improve the selectivity of a sensor 12 is to use membranes 44 selective to specific ions. Some polymeric membranes contain ionophores to allow only a specific ion (such as $Na^+$, $K^+$, $Ca^{2+}$, $Mg^{2+}$, etc.) to cross the membrane. Such membranes having selective properties are incorporated into the textile 10 to produce a device that is able to monitor a specific positive ion. In this way, the functionalized polymer fiber 14 is shielded from ions other than a specific ion to be sensed at a specific sensor 12. Table 1, below, provides examples of ionophores and selective membranes that can be used in embodiments of the present invention.

TABLE 1

Ionophore, Membrane Composition, and Selectivity Values

| Ionophore | Membrane Composition | Log $K^{POT}_{Analite/Interferent}$ | Method |
|---|---|---|---|
| <br>$K^+$ 1 (valinomycin) | $K^+$ 1 (2% wt)<br>KTpClPB (0.5% wt)<br>DOS (64.7% wt)<br>PVC (32.8% wt) | $Li^+$: −4.4<br>$Na^+$: −3.6<br>$NH_4^+$: −1.8<br>$Ca^{2+}$: −4.6 | Fixed interference method (FIM) |

TABLE 1-continued

Ionophore, Membrane Composition, and Selectivity Values

| Ionophore | Membrane Composition | Log $K^{POT}_{Analite/Interferent}$ | Method |
|---|---|---|---|
| <br>NH$_4$+ 1 (nonactin) | NH$_4$+ 1 (1% wt)<br>di-2-Ethyl-hexyl adipate (DOA) (66.8% wt)<br>PVC (32.2% wt) | Na+: −2.9<br>K+: −0.9 | Fixed interference method (FIM) |

Another way to improve the selectivity of a sensor is to use an enzyme to promote a specific reaction that allows the detection of a specific molecule. The enzyme is bonded to the functionalized polymer fiber and promotes a specific reaction with the functionalized polymer fiber. In this way, only a certain reaction that produces a specific positive ion is allowed to take place at the conductive polymer. By limiting the specific type of positive ion that is able to reach the conductive polymer, the identity of the specific molecule that triggers the reaction can be determined. For example, the enzyme of glucose oxidase could be entrapped in the textile fiber that has been functionalized with, e.g., PEDOT: PSS by using a silane molecule to bond the enzyme. In this case, the glucose oxidase will react with glucose in the sweat, producing H+ ions in proportion to the glucose molecule concentration. The H+ ions would affect the conduction of the functionalized fiber such that the enzyme textile sensor could reveal the level of glucose in the sweat.

Still another way to improve the selectivity of the sensor is to use a DNA strand bonded to the the gate electrode. This allows for the sensing of specific DNA parts present in the fluid. The DNA strand would bond with other identical DNA parts, thereby promoting the formation of the bond. Typically, DNA strands can be linked to gold electrodes (gold thin wire or textile functionalized with gold nanoparticles) by sulfonate group molecules, and in this way it is possible to prepare a gold electrode with linked DNA strands. The DNA strands can form bonds only with identical DNA parts. The device works on the capacitive change in the gate electrode. The effective potential at the gate surface change before and after the formation of DNA selective bonds, made with DNA strands that could be present in the sweat. The change in the surface potential of the electrode could be read in a change of the Ids current channel modulation. By changing the effective potential at the gate, the current gain (or transconductance) changes in proportion. In this way a textile integrated DNA sensing device is provided. Moreover, joining the control of the sweat with textile gradient structure and a DNA functionalized device, it is possible to determine the presence of specific DNA strand in the sweat, using a wearable textile device. This sensor would be able to revel specific DNA parts, such as in bacteria, to reveal contamination or infection.

Ion Selective Membrane Example

The sensing system is based on the functionalization of traditional textile fabrics, such as cotton, silk, and synthetic, with a conductive polymer sensitive to ions. The functionalized textile fiber is immersed in an ion selective membrane. The membrane includes a specific ionophore and works like an ion filter by allowing only specific ions to pass through the membrane. For example, a potassium (K+) membrane can be created using by immersing a textile in a solution containing THF solvent and high molecular weight PVC (36.5 wt. %), diisodecyl adipate (60.5 wt. %), potassium tetrakis(4-chlorophenyl)-borate (0.5 wt. %) and potassium ionophore III (2-dodecyl-2-methyl-1,3-propanediyl bis [N-[5'-nitro(benzo-15-crown-5)-4'-yl]carbamate]) (2.5 wt. %). This membrane receipt could work also with other ionophores beyond just the potassium ionophore III. For example, other ionophores include valinomycin for K+, Monensin for Na+, and Ionomycin or Calcimycine for $Ca^{2+}$ and $Mg^{2+}$. Moreover, using a ionophore like Carbonyl cyanide m-chlorophenyl hydrazone (CCCP) which is selective to H+ ions, it is possible to prepare a sensor that is sensible only to H+ concentration, that is a PH sensor. The presence of the membrane with a H+ selection on the textile polymer channel, combined with the sweat absorption and control system, allow a complete textile device that is able to determine PH in the sweat.

Figure 12:
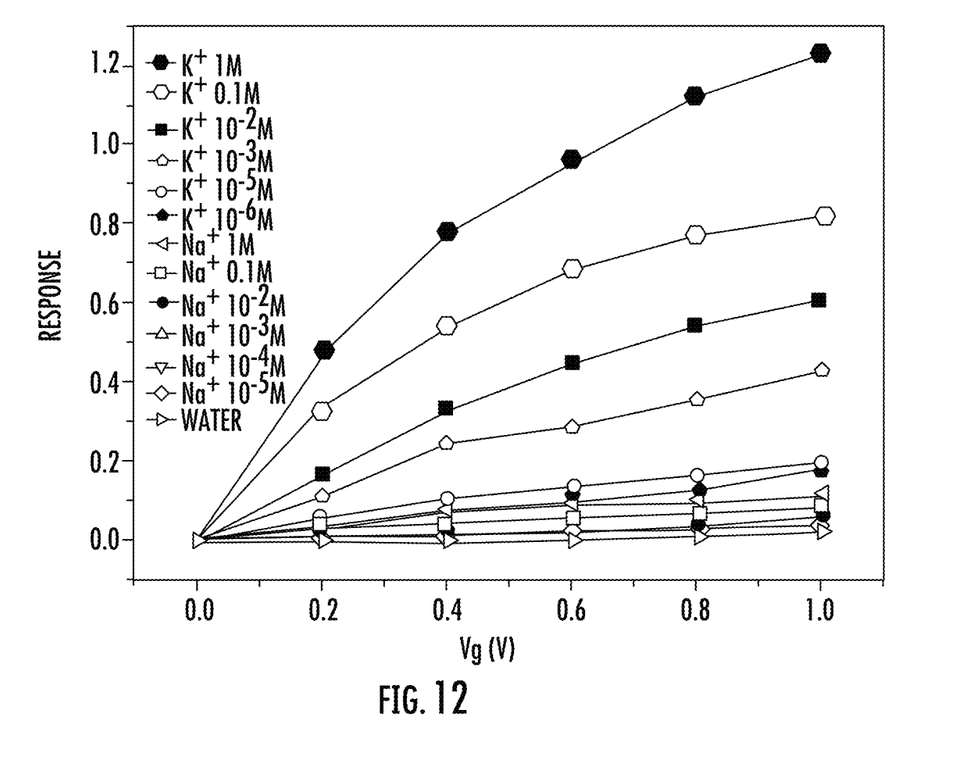
FIGS. 12 and 13 depict the response of potassium ions as compared to sodium ions for a sensor having a potassium selective membrane according to an exemplary embodiment.
Figure 13:
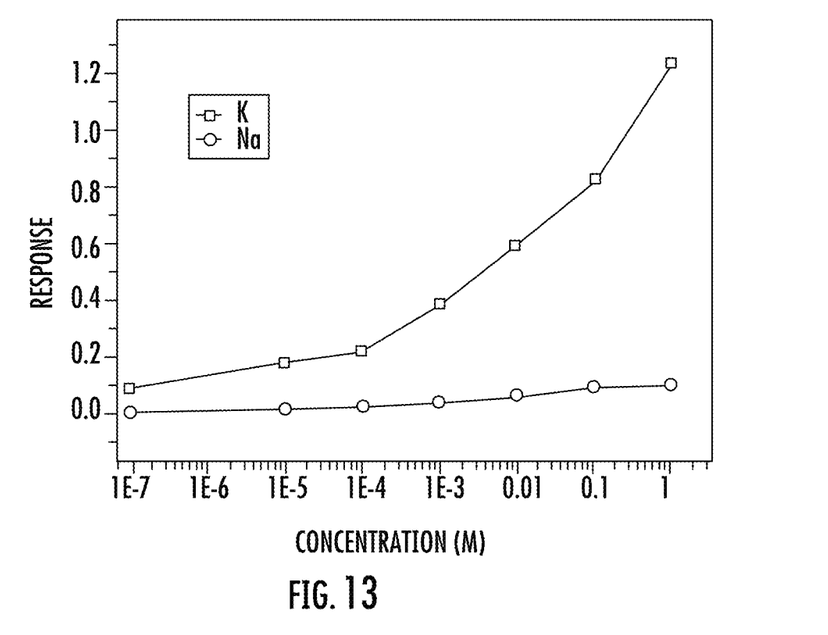

The membrane was tested to determine the selectivity of the ion membrane textile sensor in the electrochemical transistor architecture. In particular, the test determined the membrane's selectivity for potassium ions as compared to sodium ions. The results are depicted in FIG. 12. The interference comparison between sensor response ((Ids−Ids$_0$)/Ids$_0$) is shown as a function of gate potential (Vg). Potassium ion response for several different ion concentrations is shown along with sodium ion (Na+) response for several different ion concentrations. Water was used as a control substance (bottom curve). As can be seen, the modulations of K+ ions are much higher and respond to each concertation proportionally. By comparison, Na+ concentrations measurements are substantially blocked, and the curves are held much lower with no proportionality. Thus, the selectivity of the membrane is evident and allows the sensor to detect only K+ ions and not other electrolytes. Similarly, FIG. 13 shows the response curve as a function of ion concentration for a gate potential of 1V. As shown in FIG. 13, the membrane selects the K+ ions, not the Na+ ions, as evidenced by the much stronger response produced by the K+ ions.

Enzymatically Selective Membrane Example

In another embodiment, an enzyme is entrapped on a conductive polymer functionalized fiber (or on the metal gate fiber). The enzyme must be correctly adhered to the fiber to ensure accurate sensing as incorrect adhesion will allow sweat or cleaning to wash away the enzyme, thereby reducing the signal. The enzyme produces a selective reaction with a specific molecule, such as glucose, lactate, urea, dopamine, etc. (depending on the type of enzyme). The enzymatic reaction produces positive ions (such as H+) only in the presence of a specific molecule. The concentration of ions increases proportionally to with increased presence of the molecule. The sensing is most effective when the enzyme quantity is constant, which is why proper adhesion of the enzyme is important. Complicating the adhesion is the fact that the enzyme is entrapped on a fiber, which is subject to more stress and strain from movement than a typical substrate, and therefore, the enzyme has higher stability requirements. In an embodiment, a silane derivative is used to produce a network that entraps the enzyme to the polymer coated fiber such that the enzyme is not washed away.

In a specific embodiment, a percentage (from 1 to 5% in weight) of the trimethoxy[2-(7-oxabicyclo[4.1.0]hept-3-yl)ethyl]silane is added to the enzyme solution before functionalize the textile fiber. The silane molecule has the following structure:

The enzyme/silane solution is mixed with the conductive polymer solution (which includes PEDOT:PSS in this example), and the combined solution is used to swell the textile fibers. The textile fibers are heated in vacuum for approximately 1 hour at 130° C. The silane molecules reduce the swelling of PEDOT:PSS and form a network of bonds that secures the enzyme and the silane molecule on the fiber. In particular, the methoxy groups ($CH_3O-$), which are bonded to the Si atom, are the reactive part of the silane for this molecule that bonds with the conductive polymer and/or another silane during the polymerization process. The epoxy group reacts with proteins and enzymes, forming a stable bond to attach the molecule to the PEDOT:PSS.

Different enzymes could be used in the textile gradient sensors to detect different molecules specific to each sensor. For example, a glucose sensor could be provided by incorporating the glucose oxidase enzyme (of different type), using the silane molecule to entrap it in the textile fiber with the polymer. Glucose oxidase promotes a known reaction with only glucose that produces H+ ions in proportion to the quantity of glucose present in the fluid (e.g., sweat). The H+ produced in the reaction is detected by the textile gradient sensors through reduction in the conductivity of the channel of the transistor proportional to the presence of H+. Embodiments of the invention operate in accordance with the disclosure of 163605 IT, the contents of which are incorporated by reference herein in their entireties.

In another example, a lactate sensor could be provided by incorporating the lactate oxidase enzyme (of different type), using the silane molecule to entrap it in the textile fiber with the polymer. Lactate oxidase promotes a known reaction with lactate that produces H+ ions in proportion to the quantity of lactate present in the fluid (e.g., sweat). The H+ produced in the reaction could be detected by the textile gradient sensors through the reduction of conductivity of the channel of the transistor proportional to the presence of H+. Embodiments of the invention operate in accordance with the disclosure of 163605 IT, the contents of which are incorporated by reference herein in their entireties.

In still another example, a urea sensor could be provided by incorporating the urease enzyme (of different type), using the silane molecule to entrap it in the textile fiber with the polymer. Urease promotes a known reaction with urea that produces H+ ions in proportion to the quantity of urea molecules present in the fluid (e.g., sweat). The H+ produced in the reaction could be detected by the textile gradient sensors through the reduction in conductivity of the channel of the transistor proportional to the presence of H+. Embodiments of the invention operate in accordance with the disclosure of 163605 IT, the contents of which are incorporated by reference herein in their entireties.

In a further example, a dopamine sensor is provided. The dopamine sensor is designed to detect dopamine neurotransmitter by functionalizing a single cotton yarn with semiconducting polymer (PEDOT:PSS). The functionalized fiber is coated with nanostructures based on fungal laccase PDXA1b, a selective enzyme. The intensity variation of the signal together with its slope variation is used to detect the dopamine molecule in aqueous solution (e.g., sweat).

The coating of conductive PEDOT:PSS on the textile fiber is made by soaking it in aqueous solution of PEDOT:PSS. The fiber is then subjected to a heating process of 1 hour at 130° C. The functionalization with laccase enzyme is then provided by soaking the conductive polymer fiber in laccase solution. The functionalized fiber is used as a transistor channel while another conductive fiber is used as gate electrode, which modulates the current in proportion with dopamine concentration. The reaction between the dopamine molecules and laccase enzyme produces H+ ions that are measured in the organic electrochemical transistor integrated into the textile.

Figure 14:
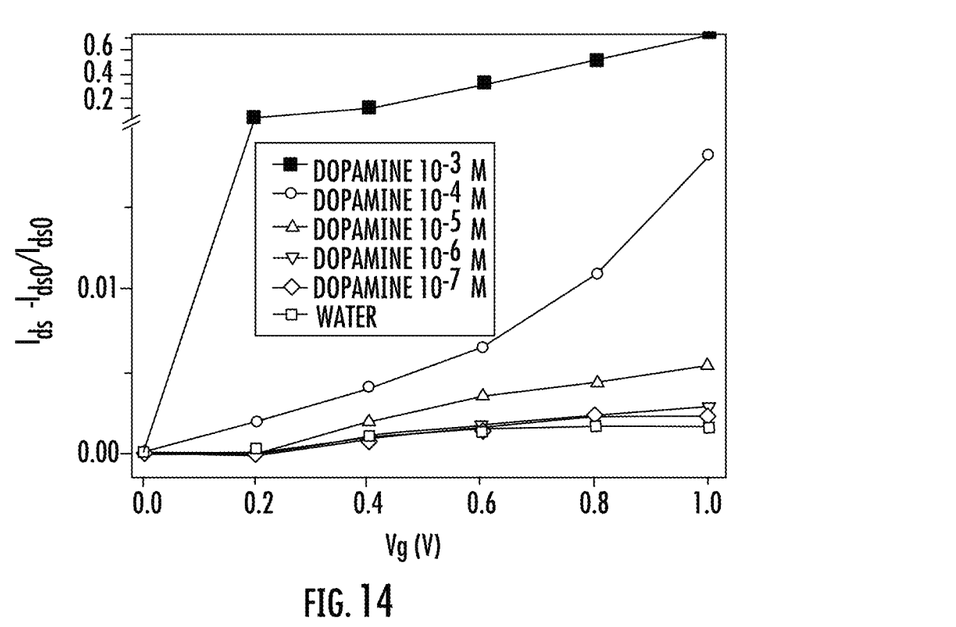
FIGS. 14 and 15 depict the response of dopamine with laccase as compared to dopamine without laccase for a sensor having a laccase selective membrane according to an exemplary embodiment.
Figure 15:
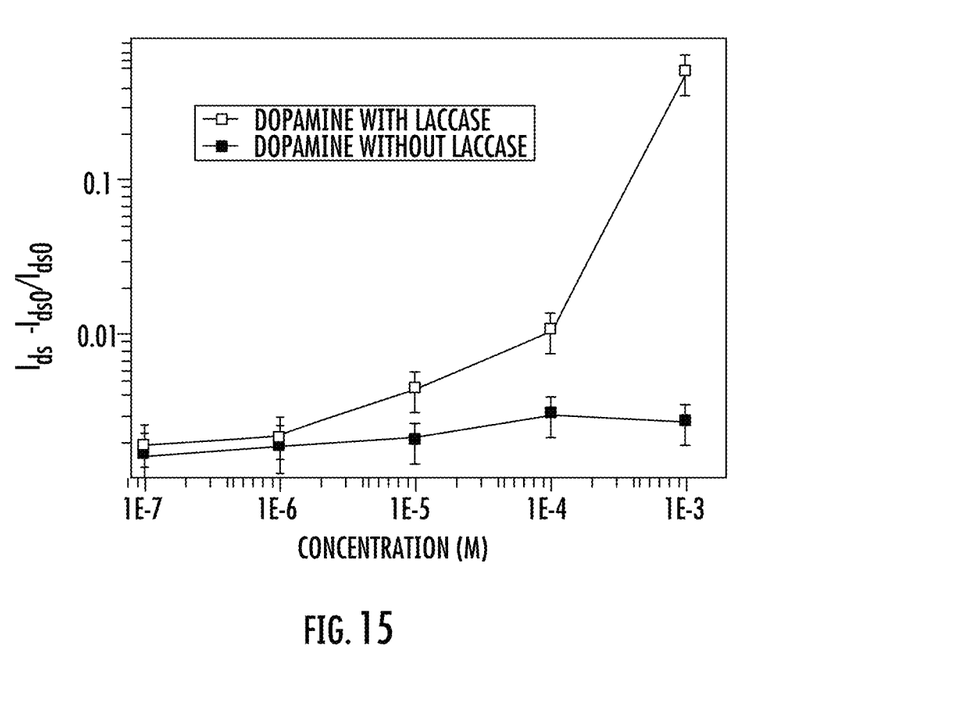

FIG. 14 depicts the response $((Ids-Ids_0)/Ids_0)$ for the dopamine sensor. As can be seen, the response is proportional to the gate voltage (Vg). As shown in FIG. 15, the response is also proportional to the concentration of dopamine for a given gate voltage potential. FIG. 15 also demonstrates that the response is predicated upon reaction with the enzyme lacasse as the response without the lacasse is much lower. Indeed, the modulation does not change much at all at different dopamine concentrations without the enzyme. Instead, with the enzyme lacasse, a reaction takes place, and the molecule becomes visible at the sensor, changing its modulation.

Figure 16:
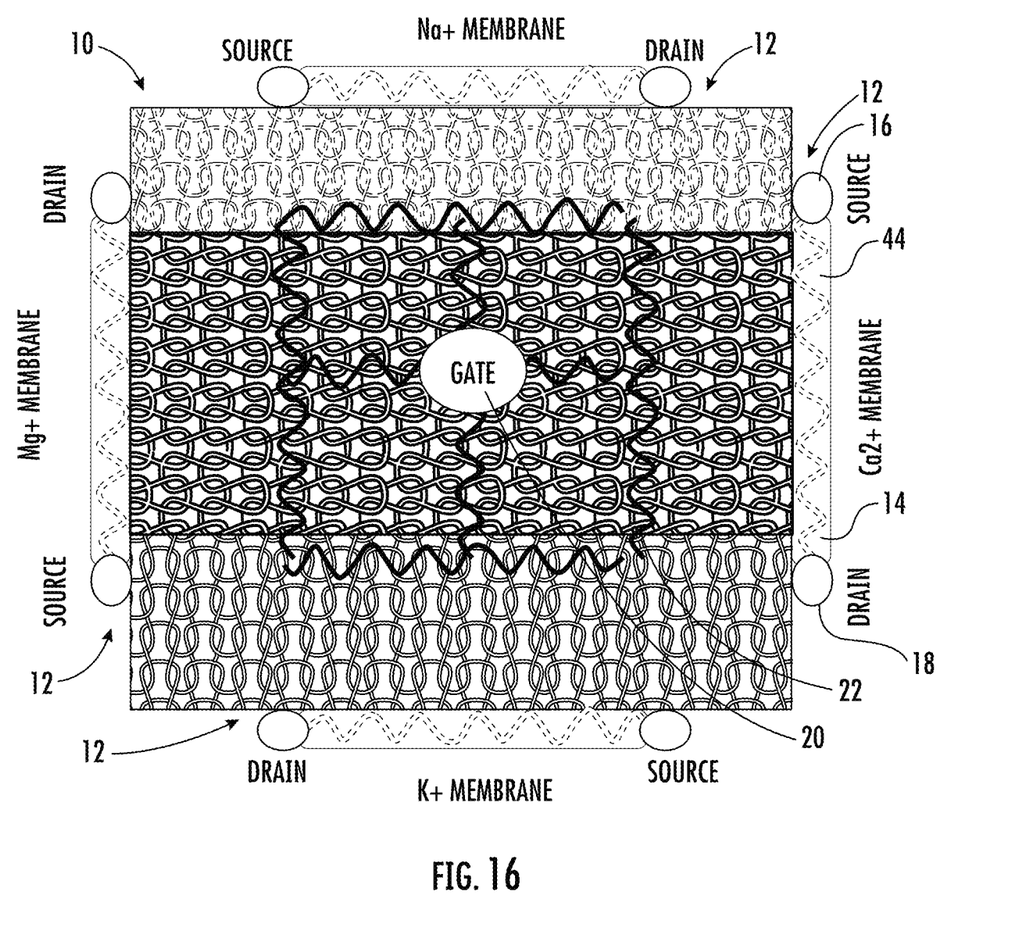
FIG. 16 depicts a textile have sensors more multiple ions integrated therein according to an exemplary embodiment.

FIG. 16 provides an array of sensors 12 integrated into a textile 10. To improve the information on a single sample of sweat, a complete analysis with different functionalized sensors 12 could give more contemporary responses to understand the effective concentrations of the solutes (i.e., ions, electrolytes, analytes, etc.) in the fluid. The idea is to use different textile fibers functionalized as channels of transistors 12 and to use a common gate 20. In this way, the currents and the potentials all reference to the same electrode. For example, to analyze the different cations contained in a series of different textile fibers functionalized with conductive polymer and ionophore membrane that have been prepared with different ionophores (Na, K, Ca, Mg) could be referenced to the same Ag-based gate electrode. In this way, the interference of each ions with respect to the other could be analyzed, and the error in the measurements could be reduced.

Figure 17:
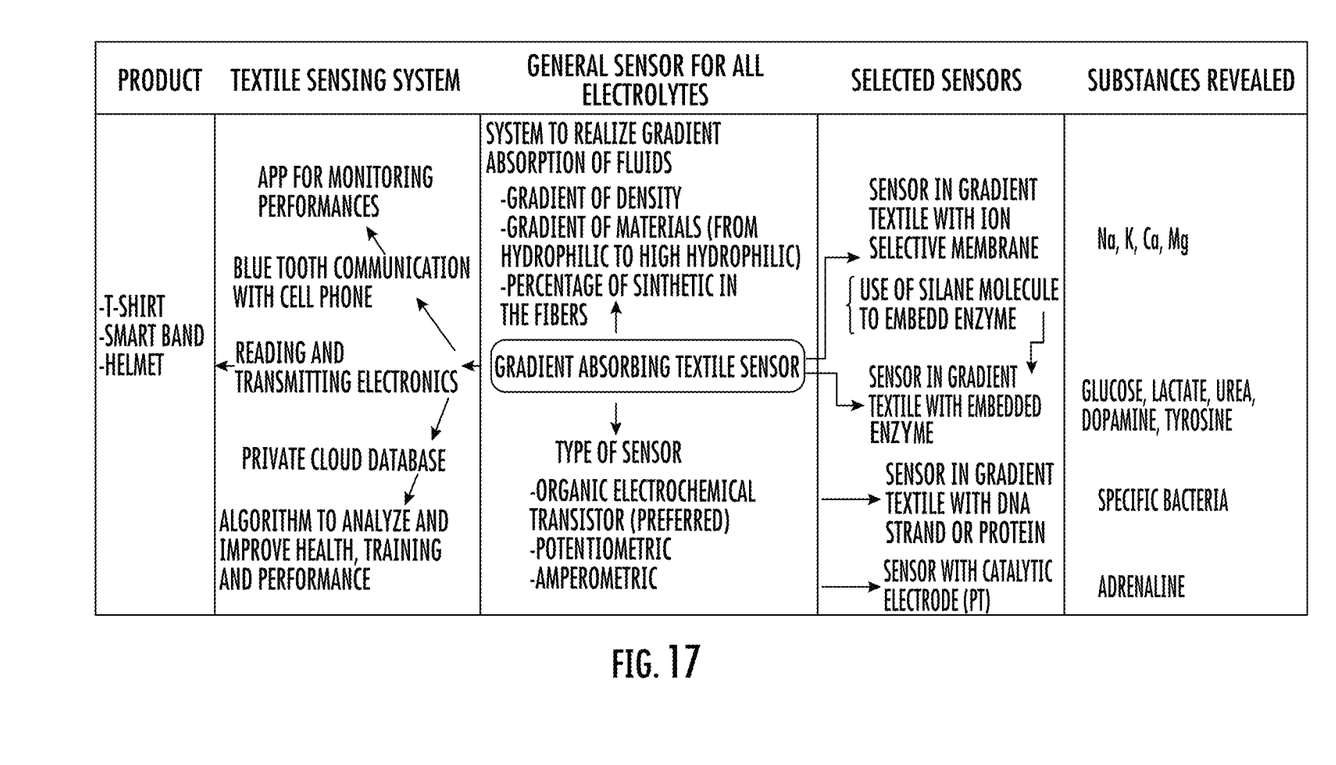
FIG. 17 depicts a relationship tree for the components of a textile sensing system according to an exemplary embodiment.

FIG. 17 provides a relationship chart between components of a sensing system. As can be seen, a product, such as a shirt, band, or helmet, is made to include a textile sensing system. The textile sensing system collects information regarding the constituents of the product wearer's sweat. In particular, the product is made at least partially of a textile according to an embodiment disclosed herein. That is, the product includes a textile have a hydrophilic gradient that directs sweat to one or more sensors. As discussed above, each sensor is preferably modified with a selective membrane, enzyme, or DNA strand so as to only admit specific ions to the functionalized fiber of the sensor. In this way, a multitude of sensors can be provided to determine the levels of several constituents in the wearer's sweat. Data collected from these sensors is exported from the product and displayed on, e.g., a mobile application of a cellular device. Additionally, the data can be exported from the mobile application or directly from the product to a cloud service where it can be stored and accessed across a variety of platforms. For example, an athletic trainer can analyze the data being collected from a trainee so as to monitor the electrolyte and hydration levels of the trainee.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A textile, comprising:
    a hydrophilic region, the hydrophilic region having a gradient of hydrophilicity from a first end of lower hydrophilicity to a second end of higher hydrophilicity;
    a hydrophobic region surrounding, at least in part, the hydrophilic region;
    at least one sensor woven into the hydrophilic region, each of the at least one sensor having a source electrode, a drain electrode, and a gate electrode, wherein the source electrode and the drain electrode are connected by a first fiber and the gate electrode is connected to a second fiber.

2. The textile of claim 1, wherein the first fiber is a conductive polymer or is a fiber functionalized with a conductive polymer.

3. The textile of claim 2, wherein the conductive polymer is at least one of poly(3,4-ethylenedioxythiophene), poly(6-(thiophene-3-yl)ethane-1-sulfonate, polyaniline, polypyrrole, polythiophene, or polyfuran.

4. The textile of claim 1, wherein the second fiber has metal deposited thereon, is functionalized with metal particles, is functionalized with a conducting polymer, is a metal thread, or is a carbon fiber.

5. The textile of claim 1, wherein the first fiber is coated with an ion-selective membrane.

6. The textile of claim 5, wherein the ion-selective membrane only allows one ion selected from the group consisting of $Na^+$, $K^+$, $Ca^{2+}$, $Mg^{2+}$ to pass through to the first fiber and the second fiber.

7. The textile of claim 1, wherein the hydrophilic region includes hydrophilic fibers of a first material and wherein the gradient of hydrophilicity is created by increasing a percentage of hydrophilic fibers going from the first end to the second end.

8. The textile of claim 1, wherein the gradient of hydrophilicity is created by changing a packing density of a textile fiber in the hydrophilic region from a lower density at the first end to a higher density at the second end.

9. The textile of claim 1, wherein of the first fiber is provided with an enzymatically selective membrane.

10. The textile of claim 9, wherein the enzymatically selective membrane includes at least one of glucose oxidase, lactate oxidase, urease, or laccase.

11. The textile of claim 9, wherein the enzymatically selective membrane is configured to select one of glucose, lactate, urea, or dopamine for detection by the at least one sensor.

12. The textile of claim 1, comprising at least two sensors, wherein each sensor is configured to detect a different analyte.

13. The textile of claim 12, wherein each of the at least two sensors have a common gate electrode.

14. A wearable product, comprising the textile of claim 1.

15. The wearable product of claim 14, wherein the wearable product is a shirt, a band, or a helmet.

16. The textile of claim 1, wherein the gradient of hydrophilicity comprises at least four grades of increasing hydrophilicity between the first end and the second end.

* * * * *

UNITED STATES PATENT AND TRADEMARK OFFICE
CERTIFICATE OF CORRECTION

PATENT NO. : 11,344,230 B2
APPLICATION NO. : 15/942658
DATED : May 31, 2022
INVENTOR(S) : Nicola Coppede et al.

It is certified that error appears in the above-identified patent and that said Letters Patent is hereby corrected as shown below:

In the Claims

Claim 6, Line 3 reads "of $Na^+$, $K^+$, $Ca^{2+}$, $Mg^{2+}$ to pass through to the first fiber and" and should read – of $Na^+$, $K^+$, $Ca^{2+}$, and $Mg^{2+}$ to pass through to the first fiber and –

Signed and Sealed this
Sixteenth Day of August, 2022

Katherine Kelly Vidal
*Director of the United States Patent and Trademark Office*